United States Patent [19]

Klapwijk et al.

[11] Patent Number: 5,017,496

[45] Date of Patent: May 21, 1991

[54] METHOD FOR DETERMINING THE RESPIRATION RATE OF A RESPIRING MATERIAL IN THE FORM OF A CONTINUOUS PROCESS CURRENT, AS WELL AS A DEVICE SUITABLE FOR SUCH AN APPLICATION

[75] Inventors: Abraham Klapwijk, Bennekom; Henricus L. F. M. Spanjers, Oss, both of Netherlands

[73] Assignee: Ecotechniek B.V., Beneluxlaan, Netherlands

[21] Appl. No.: 123,109

[22] PCT Filed: Feb. 13, 1987

[86] PCT No.: PCT/NL87/00004

§ 371 Date: Oct. 15, 1987

§ 102(e) Date: Oct. 15, 1987

[87] PCT Pub. No.: WO87/05114

PCT Pub. Date: Aug. 27, 1987

[30] Foreign Application Priority Data

Feb. 17, 1986 [NL] Netherlands .......................... 8600396

[51] Int. Cl.⁵ ................... G01N 33/18; G01N 33/483

[52] U.S. Cl. ..................................... 436/62; 422/68.1; 422/79; 436/136; 436/138

[58] Field of Search .......................... 422/68, 79, 68.1; 435/4; 436/62, 136, 138; 204/403; 210/96.2

[56] References Cited

U.S. PATENT DOCUMENTS 3,731,522 5/1973 Mikesell ..................... 73/19
3,813,325 5/1974 Merrell et al. .................. 204/195 B Primary Examiner—Robert J. Warden
Assistant Examiner—Jill Johnston
Attorney, Agent, or Firm—Harness, Dickey & Pierce

[57] ABSTRACT

Method and device for determining the respiration rate of a respiring material such as active sludge in a continuous process flow before and after holding thereof in a respiration chamber. The oxygen content in the continuous process current is done at a single measurement point. This is done by reversing the incoming and outgoing current of the respiration chamber. Preferably the process flow consists of a mixture of respiring material and waste water to be biologically purified.

9 Claims, 1 Drawing Sheet

METHOD FOR DETERMINING THE RESPIRATION RATE OF A RESPIRING MATERIAL IN THE FORM OF A CONTINUOUS PROCESS CURRENT, AS WELL AS A DEVICE SUITABLE FOR SUCH AN APPLICATION

As is known, oxygen-consuming biochemical reactions such as substrate oxidation, nitrification, and formation and degradation of cell material and reserve substances take place in an active sludge suspension. These reactions result in an overall oxygen consumption of the suspension and the rate at which said oxygen consumption takes place is therefore a good measure of the biological activity of the sludge. The rate, expressed in mass of oxygen per unit volume and unit time is termed respiration rate.

For the purpose of biological waste water purification it is of importance to be able to measure the respiration rate of active sludge. This can be illustrated by a few examples:

The respiration rate may be used as a basis for a better process control. Thus, an optimum matching of the aeration to the oxygen consumption makes it possible, on the one hand, to save energy costs for the aeration and, on the other hand, to match the effluent quality to the standards imposed thereon.

A sudden decrease in the respiration rate measured in a small-scale test reactor in which partial flows of influent and return sludge are combined is an indication that the influent has an acutely toxic effect on the active sludge. This observation may then result in actions which prevent process breakdown.

In the investigation of the toxicity and a biological degradability of environmentally extraneous substances in active sludge, measurement of the respiration rate will provide important information.

The above examples imply the desirability of a reliable continuous method of measuring the respiration rate which preferably can be used on line with a view to automation.

Methods of measurement known from the state of the art are the methods using the manometric principle, i.e. based on the measurement of the volume of oxygen consumed. Since the introduction of the manometric respiration measurement, various methods have been conceived for improving said measurement. The most well-known embodiment is the Warburg one (Jenkins, D., 1960, "The use of manometric methods in the study of sewage and trade wastes" in: Waste Treatment, Pergamon Press, New York), in which the volume of gas is kept constant. General disadvantages of the manometric methods are:

sensitivity to temperature and pressure fluctuations,
the performance of the measurement is time-consuming and requires considerable experience, and
unsuitability for continuous application and automation.

After the introduction of the amperometric oxygen concentration measurement by means of the Clarck cell (Mancy K. H., Okun D., and Reilley C. N., 1962, "A galvanic cell oxygen analyser"; J. Electroanal. Chem., 4, 65–92), the manometric methods have been superseded by the electrochemical respiration measurements. These are based on measuring the concentration of dissolved oxygen in an active sludge suspension. The measurement of the oxygen concentration is relatively simple and lends itself to on-line applications. It is possible to correct for the effects of temperature and pressure fluctuations in a relatively simple manner. A distinction can broadly be made between two methods: the batchwise or "closed" respiration measurement and the continuous or "open" respiration measurement.

Batchwise methods are the most used. In this case, the respiration rate is determined by measuring the rate of decrease of the oxygen content in a sludge sample after switching off the aeration and sealing it off from the atmosphere (Stack, V. T., 1970, "Method and apparatus for measuring rate of consumption of dissolved gas in a liquid"; U.S. Pat. No. 3,510,406, and Pagge, U., and Günthner W., 1981, "The BASF toximeter—a helpful instrument to control and monitor biological waste water treatment plants"; Wat. Sci. Tech., 13, 233–238). However, said method has the disadvantage that continuous measurements are not possible.

In an open respirometer aeration takes place. An equilibrium is established between the supply and the consumption of oxygen. If the oxygen supply coefficient (Kla) is known, the respiration rate can be calculated directly from the measured oxygen concentration (Farkas, 1969, "Method for measuring aerobic decomposition activity of activated sludge in an open system'-'—Advances in Water Pollution Research, 4th Int. Conf. Prague, April 21–25, 1969 (edited by Jenkins) Pergamon Press, London, Dec. 4, 1969, pages 309–317, 319–327; Holmberg U. and Olsson G., 1985, "Simultaneous estimation of oxygen transfer rate and respiration rate"; Modelling and control of biotechnological processes, Preprints/ Proceedings 1st IFAC Symposium, Noordwijkerhout, Dec. 11–13, 1985). The value of Kla can in principle be determined by experimental sampling. The problem in this case is, however, that said quantity depends on various process factors and, in addition, is a function of the respiration rate.

Closed respirometers are also known in which the respiration rate is determined by allowing active sludge or comparable respiring materials, such as liquids containing oxygen-consuming bacteria, to flow through a completely closed respiration vessel, the oxygen concentration of the incoming and of the outgoing flow of the vessel being measured. The problem in this case is the accuracy of the separate oxygen sensors in the incoming and outgoing flow respectively (Mikesell R. D., (1973), "Method and apparatus for determining oxygen consumption rate in sewage", U.S. Pat. No. 3,731,522; Merrell K. C., et al. (1974), "Continuous respirometer apparatus", U.S. Pat. No. 3,813,325).

FIG. 1 shows an embodiment of such a prior art continuous respirometer. A supply line 10 delivers an active sludge solution to it at a flow rate 2 to a repiration chamber 2, such as a vessel, completely sealed from the atmosphere and having a capacity V to fill this chamber. Just before the suspension is fed into said chamber, the oxygen content is measured by means of an oxygen measuring cell $C_1$ indicated at 15 and the same measurement is performed by an oxygen measuring cell $C_2$ indicated at 16 when the suspension leaves the unaerated chamber through a drain line 11 under the influence of a pump 14. The theoretical average residence time can be determined using the formula $V/Q$ and the respiration rate by means of the formula $(C_1-C_2) Q/V$. A prerequisite for such a measurement is that the oxygen content of the suspension should be sufficiently high, it being assumed that the content of the unaerated chamber may be regarded as ideally mixed.

It has been found, however, that two separate oxygen measuring cells may exhibit a different response characteristic and ageing pattern.

SUMMARY OF THE INVENTION

It has been found that the disadvantages known from the state of the art outlined above to effect the electrochemical respiration measurements can be eliminated if the respiration rate is determined by measuring the oxygen content in the continuous process flow, which consists of respiring material, before and after residence thereof in a respiration chamber, which is completely filled with liquid and sealed off from the atmosphere, at a single measuring point in the incoming and outgoing current respectively of the respiration chamber in relation to the process current fed in or fed back.

DETAILED DESCRIPTION OF THE PREFERRED EMBODIMENTS OF THE INVENTION

Figure 1:
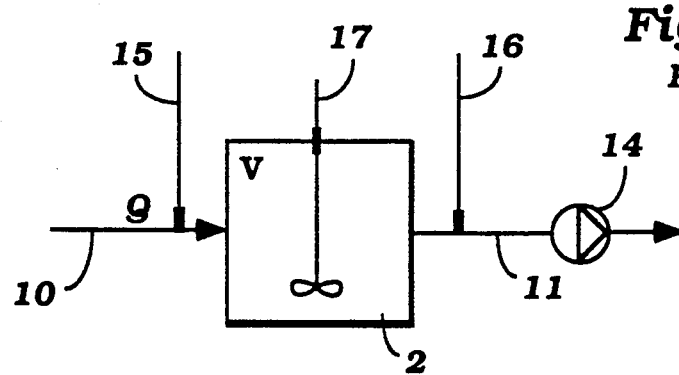
FIG. 1 is a schematic view of a system operating in accordance with the prior art.
Figure 2:
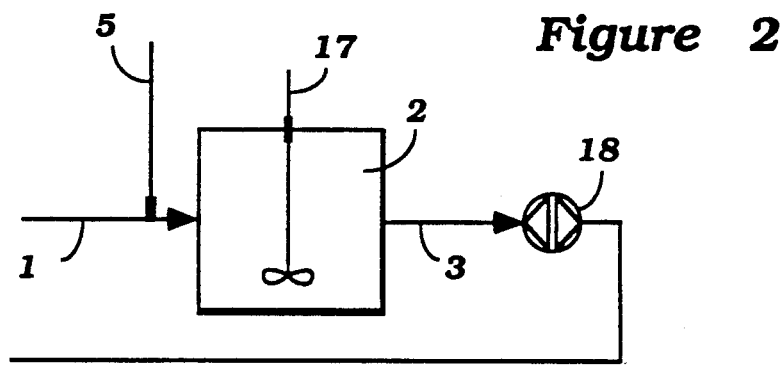
FIG. 2 is a schematic view showing a system functioning in accordance with an embodiment of the invention.

FIG. 2 shows schematically a device for carrying out the method of measurement according to the invention. In addition to the unaerated respiration chamber, 2 for example a vessel, which is provided with supply line 1 and drainage line 3 in which a reversible pump 18 is provided, the device comprises an oxygen measuring cell inserted next to said chamber as indicated schematically at 5 and the pump 18 with a reversible direction of rotation. By pumping the sludge suspension alternately in both directions, the oxygen content is measured in turn in aerated sludge and in sludge which has not been aerated for a (residence) time. The respiration rate can be calculated in the manner described above.

Another embodiment is based on reversing the direction of flow by means of a valve switching system. Any problems in measuring the oxygen concentration can be eliminated by stirring the liquid below the oxygen measuring cell by a stirrer indicated by the reference numeral 17.

An important aspect in the precise interpretation of the measurement data is the hydraulic behaviour of the measuring system according to the invention. The reason for this is that the sludge in the vessel reflects a situation which always lags behind the situation in the fresh sludge by a residence time and cannot therefore be compared with it as such. The hydraulic behaviour is determined by measurements of residence time. Once the hydraulic model has been established, the respiration rate can be determined at any instant from the measured oxygen concentration.

Moreover, it is known from the literature that the measurement of the respiration rate is used to obtain an insight into the actual oxygen consumption of an aeration tank in a waste water purification plant. Said measurement may be performed, for example, in accordance with the standard entitled "Bestimmung der Sauerstoffverbrauchsrate" ("Determination of the Oxygen Consumption Rate"), DIN 38,414, Part 6, "Deutsche Einheitsverfahren zur Wasser-, Abwasser- und Schlammuntersuchung" ("German Standard Methods for the Examination of Water, Waste Water and Sludge"). In this connection, G. Reinnarth and H. Rüffer (1983) (Bestimmung der Sauerstoffverbrauchsraten von Belebtschlamm) (Determination of the Oxygen Consumption Rates of Activated Sludge, Vom Wasser 60, 223-235) recommend aerating the sludge sample as rapidly as possible and then measuring the drop in the oxygen concentration. A continuous withdrawal of active sludge followed by residence in a closed respiration vessel should then yield the oxygen consumption in the aeration tank.

It has been found, however, that a continuous withdrawal of active sludge from an aeration tank does not immediately yield the respiration rate in the aeration tank. In principle, said measurement yields only the endogenous respiration rate along with the oxygen consumption as a result of the oxidation of substances still dissolved in the water. If active sludge is withdrawn from an aeration tank in which the load is below the maximum capacity, the respiration rate measured in the respiration vessel will be lower (for example, 20 to 30% or more) than the respiration rate in the aeration tank.

According to a special embodiment of the invention, the abovementioned problem is solved in that a mixture of respiring material and waste water to be biologically purified is used as the process current in the respiration chamber. Preferably, a mixture of respiring material and waste water to be biologically purified is in this case used as process current which is such that the volume of the respiration chamber completely filled with liquid divided by the rate of flow of the waste water supplied to the chamber is equal to the volume of the aeration tank from which the process current is withdrawn divided by the rate of flow of the waste water supplied to the aeration tank.

Figure 3:
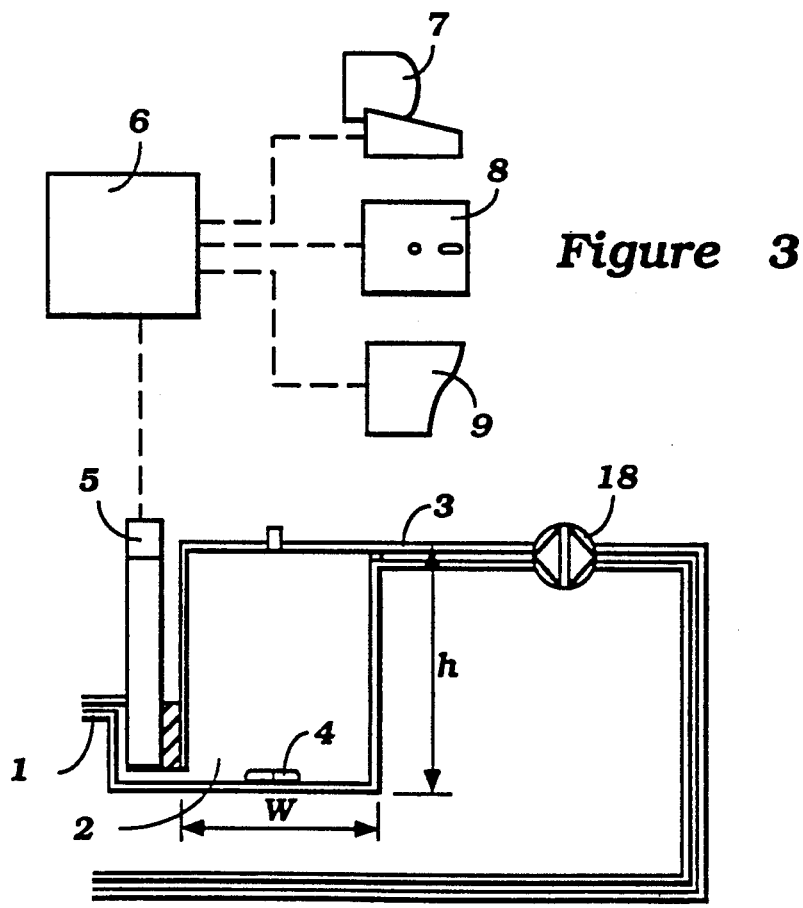
FIG. 3 is a diagrammatic view showing the measurement arrangement in accordance with an embodiment of the invention.

The respirometer according to the invention can be coupled to a digital measuring and regulation system (for example, Siemens SMP modular system) which provides for the measurement of oxygen concentration, the calculation of the respiration rate and the regulation of the frequency with which the direction of rotation of the pump is reversed. The maximum frequency of reversal is determined by the rate at which the signal from the oxygen measuring cell reaches an equilibrium value. The possibility of automatically correcting the measured value of the oxygen concentration for changes in atmospheric pressure is incorporated in the control program. FIG. 3 shows a diagram of the measurement arrangement in which (1) denotes the supply line of an unaerated vessel, (2) denotes the unaerated vessel, (3) denotes the drain line from the unaerated vessel, (4) denotes a magnetic stirrer, (5) denotes the oxygen measuring cell, (6) denotes the SMP system, (7) denotes a keyboard and monitor coupled to said system, (8) denotes a data storage bank and (9) denotes a printer.

The presence of computer facilities makes it possible to determine quantities related to the respiration rate in an indirect manner. Thus, the biochemical oxygen consumption of a waste water can be calculated by integrating the measured respiration rate with respect to time. Moreover, it is possible to perform on-line process regulation on the basis thereof.

We claim:

1. A method for determining the respiration rate of a respiring material contained in a continuous process flow by measuring the oxygen content in the continuous process flow before and after residence of the continuous process flow in a respiration chamber sealed off from the atmosphere, comprising the steps of measuring the oxygen content in the continuous process flow at a single measurement location by passing the continuous process flow in a first direction past the single measurement location and taking a first measurement of the oxygen content in the continuous process flow just before the continuous process flow enters the chamber and then, after residence of the continuous process flow in the chamber, reversing the continuous process flow past the single measurement location in a second direction and taking a second measurement of the oxygen content in the continuous process flow before continuing the movement of the continuous process flow in the first direction.

2. The method according to claim 1, wherein the oxygen content is measured at the single measurement location by an oxygen measuring cell and wherein the continuous process flow is reversed at a frequency sufficient for the oxygen measuring cell to achieve an equilibrium.

3. The method according to claim 1, wherein a mixture of respiring material and waste water to be biologically purified is used as the continuous process flow.

4. The method according to claim 3, wherein the volume of the chamber completely filled with liquid divided by the rate of flow of the waste water fed to the chamber is equal to the volume of an aeration tank from which the continuous process flow is withdrawn divided by the rate of flow of the waste water supplied to aeration tank.

5. The method according to claim 1, wherein the respiring material is active sludge.

6. A device for determining the respiration rate of a respiring material in a continuous process flow by means of measuring the oxygen content in the continuous process flow before and after residence of the continuous process flow in a respiration chamber, which is completely filled with liquid and sealed off from the atmosphere, comprising at least a supply line for the continuous process flow, a respiration chamber in communication with said supply line free of aeration elements and sealed off from the atmosphere, at least a drainage line for the continuous process flow in communication with and leading from said chamber, an oxygen measuring cell positioned next to said chamber and means for sequentially reversing the continuous process flow through said respiration chamber.

7. The device according to claim 6 wherein the means for sequentially reversing the continuous process flow comprises a valve switching system fitted in the supply and drainage lines.

8. The device according to claim 6, further comprising a digital measuring and regulating system coupled to the oxygen measuring cell for measuring the oxygen concentration, calculating the respiration rate of the respiring material and regulating the frequency at which the means for sequentially reversing the flow is reversed.

9. The device according to claim 6, further comprising a computer control unit for performing on-line process regulation and control.

* * * * *